United States Patent
Vad

(10) Patent No.: US 6,527,760 B1
(45) Date of Patent: Mar. 4, 2003

(54) OUT-PATIENT JOINT LAVAGE KIT AND PROTOCOL

(76) Inventor: Vijay B. Vad, 1365 York Ave. #5F, New York, NY (US) 10021

(*) Notice: Subject to any disclaimer, the term of this patent is extended or adjusted under 35 U.S.C. 154(b) by 163 days.

(21) Appl. No.: 09/669,054

(22) Filed: Sep. 25, 2000

(51) Int. Cl.$^7$ ............................................. A61M 31/00
(52) U.S. Cl. ...................................... 604/512; 604/522
(58) Field of Search .......................... 604/512, 46, 518, 604/522

(56) References Cited

U.S. PATENT DOCUMENTS

| | | | |
|---|---|---|---|
| 4,195,368 A | 4/1980 | Patrichi .......................... | 3/1.91 |
| 4,294,251 A | 10/1981 | Greenwald et al. .......... | 128/276 |
| 4,402,331 A | 9/1983 | Taldo et al. ............... | 134/58 R |
| 4,523,679 A | 6/1985 | Paikoff et al. ............... | 206/370 |
| 4,582,685 A | 4/1986 | Guadagno et al. ............. | 422/61 |
| 4,595,102 A | 6/1986 | Cianci et al. ................ | 206/572 |
| 4,872,866 A | 10/1989 | Davis .......................... | 604/227 |
| 5,330,424 A | 7/1994 | Palmer et al. ................. | 604/28 |
| 5,558,646 A | 9/1996 | Roche .......................... | 604/143 |
| 5,836,907 A | 11/1998 | Campbell ..................... | 604/27 |
| 5,881,733 A | 3/1999 | Stone .......................... | 128/898 |
| 5,921,987 A | 7/1999 | Stone .......................... | 606/80 |
| 5,931,820 A | 8/1999 | Morse ......................... | 604/283 |
| 5,964,728 A | 10/1999 | Lin .............................. | 604/30 |
| 6,012,586 A | 1/2000 | Misra .......................... | 206/571 |
| 6,021,534 A | 2/2000 | Koch ............................ | 5/606 |
| 6,106,506 A | 8/2000 | Abell et al. .................. | 604/275 |
| 6,110,209 A | 8/2000 | Stone ....................... | 623/16.11 |

OTHER PUBLICATIONS

Peyron, Jacques G., *Intraarticular Hyaluronan Injections in the Treatment of Osteoarthritis: State–of–the–Art Review*, The Journal of Rheumatology, pp. 10–15, vol. 20, Supplement 39, 1993. Supplement 39.

Scale, D., et al., *Viscosupplementation of Osteoarthritic Knees with Hylan: A Treatment Schedule Study*, Current Therapeutic Research, pp. 220–232, vol. 55, No. 3, Mar. 1994.

Adams, Mark E., et al., *The Role of Viscosupplementation with Hyland G–F 20 (Synvisc®) in the Treatment of Osteoarthritis of the Knee: A Canadian Multicenter Trial Comparing Hylan G–F 20 Alone, Hylan G–F 20 with Non–Steroidal Anti–Inflammatory Drugs (NSAIDs) and NSAIDs Alone*, Osteoarthritis and Cartilage, p. 213–225, vol. 3, No. 4, Dec. 1995.

Chang, Rowland W., et al., *A Randomized, Controlled Trial of Arthroscopic Surgery Versus Closed–Needle Joint Lavage for Patients with Osteoarthritis of the Knee*, Arthritis and Rheumatism, pp. 289–296, vol. 36, No. 3, Mar. 1993.

Ike, Robert W., et al., *Tidal Irrigation Versus Conservative Medical Management in Patients with Osteoarthritis of the Knee: A Prospective Randomized Study*, The Journal of Rheumatology, pp. 772–779, vol. 19, 1992.

*Local Medical Review Policy for Hylan Polymers for Treatment of Osteoarthritis New Policy*, CPT Physicians' Current Procedural Terminology, American Medical Association, Apr. 1999.

Website search results from http://www.virtualdrugstore.com/osteoarthritis/hylan.html for Hylan G–F 20.

Website search results from http://coninfo.nursing.uiowa.edu/sites/pedspain/Adjuvants/Hyalgatt.htm for Synvisc Hylan G–F 20.

Website search results from http://www.almedicare.com/provider/integrity/policy B/1–79999–15.htm for Sodium Hyaluronate—Hyalgan 20 mg (2cc)—Synvisc (hylan G–F 20) 16 mg (2cc).

*Primary Examiner*—Manuel Mendez
*Assistant Examiner*—Mark Han
(74) *Attorney, Agent, or Firm*—Bierman, Muserlian and Lucas

(57) ABSTRACT

Out-patient knee lavage is performed by use of a kit comprising:

A. Means for preparing the knee joint for lavage;
    B. An optional surgical drape;
    C. A first needle and a first syringe containing a first local anesthesia;
    D. A second needle and second syringe containing a second local anesthesia; and
    E. A third syringe adapted to fitting the second needle, the third syringe containing a lavage fluid.

The knee lavage is performed by:

1. Cleansing the knee joint and, preferably, covering it with a surgical drape;
2. Applying the first local anesthesia superficially to the joint to create a wheat;
3. Injecting through the wheal the second local anesthesia into the knee joint; and
4. Performing the lavage on the knee joint without removing the second needle from the knee joint.

6 Claims, No Drawings

OUT-PATIENT JOINT LAVAGE KIT AND PROTOCOL

FIELD OF THE INVENTION

This invention relates to lavage. In one aspect, the invention relates to a kit for performing a joint, e.g., knee, lavage in an out-patient setting while in another aspect, the invention relates to a protocol for performing a joint lavage in an out-patient setting. In yet another aspect, the invention relates to a protocol for the treatment of osteoarthritis of the knee by using knee lavage in combination with sodium hyaluronate or hylan.

BACKGROUND OF THE INVENTION

Osteoarthritis of the knee is an ailment common to a large segment of the elderly population of the United States. Pain and diminished function are common traits of the ailment, and various protocols exist for the treatment of this ailment. Total knee arthroplasty has proven successful for patients with end-stage osteoarthritis of the knee but due to its expense and relatively high failure rate for those patients with active lifestyles, it has not been as available and/or successful for patients with non-end-stage osteoarthritis of the knee. For this latter group of patients, protocols employing hylan or sodium hyaluronate have demonstrated considerable success.

Hyaluronic acid is a natural constituent of synovial fluid and cartilage. The function of the hyaluronic acid is to maintain structural and functional characteristics of extracellular matrix and fluids. Presently two products are composed of various fractions of hyaluronate are approved by the United States Food and Drug Administration for relief of pain associated with osteoarthritis of the knee for patients who have failed to respond adequately to conservative nonpharmacologic therapy and simple analgesics. These products are sodium hyaluronate sold under the trademark HYALGAN™ and hylan-G-F-20 sold under the trademark SYNVISC™. Both of these products are classified as prosthetic devices. Various protocols exist for use of these products, and a typical protocol for sodium hyaluronate is a series of injections over five weeks. For hylan-G-F-20, a typical protocol is a series of injections over three weeks.

One limitation on these treatments of non-end-stage osteoarthritis of the knee is the cost associated with the performance of this procedure in a hospital setting. As is well known, the cost associated with just about any medical procedure performed within a hospital setting as compared to the procedure performed in an out-patient setting (i.e., an out-patient clinic, a physician's office, a patient's home, etc.) is often much larger. As such, a recognized need exists for a joint lavage kit and protocol for use in an out-patient setting in order to minimize expenses and complications such as infections. Moreover, the medical profession has a continuing interest in improving any of the existing protocols for treatment of osteoarthritic joints.

SUMMARY OF THE INVENTION

In one embodiment of this invention, a kit is provided for performing an out-patient joint lavage, the kit comprising:
A. Means for preparing the joint for the lavage;
B. A first needle fitted with a first syringe containing a local anesthesia;
C. A second needle for conducting the lavage;
D. A second syringe containing a second anesthesia; and
E. A third syringe containing a lavage fluid.
E. A third syringe containing a lavage fluid.

Optional components of the kit include a sterile container in which components A-E are packaged for shipment and storage; a sterile drape with a cut-out hole to cover the joint during the lavage procedure; sterile gloves, mask and hat for the attending physician; and additional needles, syringes, anesthesia and lavage fluid.

In another embodiment of the invention, the out-patient joint lavage procedure or protocol comprises the steps of:
A. Preparing the joint by cleaning and/or sterilizing the covering skin of the joint;
B. Covering the prepared joint with a sterile drape, the drape having a cut-out hole that is positioned over the joint such that the area of skin through which the joint will be entered is exposed to the attending physician;
C. Applying a first anesthesia superficially to the joint to create a wheal;
D. Injecting intra-articular a second anesthesia through the wheal; and
E. Performing a lavage on the joint.

The first anesthesia is applied using a relatively small needle which is removed after injection of the anesthesia. The second anesthesia is injected using a larger needle which remains in the joint to maintain a closed system. The syringe containing the second anesthesia is replaced with a syringe containing the lavage fluid, e.g., normal saline in combination with an antibiotic. After the lavage fluid is injected into the joint, it is slowly aspirated back into the syringe and if any additional fluid is to be removed from the joint, e.g., excess synovial fluid and debris, it can be aspirated into the syringe (at least partially) which was used to inject the second anesthesia. Of course, prior to performing the procedure the attending physician has donned appropriate sterile dress, e.g., sterile hat, gloves and mask, and has covered the cleansed skin over the joint with an appropriate sterile drape.

In another embodiment of the invention, the lavage protocol described above is used in combination with a sodium hyaluronate or hylan G-F-20 protocol. In this embodiment, the lavage protocol is performed on the joint prior to the sodium hyaluronate or hylan G-F-20 protocol.

DETAILED DESCRIPTION OF THE INVENTION

Although the following description of the various embodiments of this invention are in terms of a knee lavage, the kit and protocols of this invention are also applicable to other joints, both human and animal. Other joints include elbow, shoulder, hip, ankle, wrist and digit. Animals other than human for which the kit and protocol have utility include most mammals. In addition, although the following description of the various embodiments of the invention are in terms of the treatment of osteoarthritis, the kit and protocols of this invention also have applicability to joints suffering other ailments in which a lavage is deemed an appropriate treatment by a trained physician or veterinarian.

The joint lavage protocol of this invention is a closed needle lavage. By "closed needle lavage" is meant that the lavage fluid is injected into the joint through a needle from a syringe and the same needle and syringe are used to recapture the lavage fluid along with any synovial fluid and debris loosened by the lavage fluid. In other words, the lavage can be completed with one needle penetration of the joint.

With respect to the kit, the means for preparing the joint for the lavage can comprise any conventional pads or swabs typically used for cleansing and/or sterilizing an area of skin over which an incision or injection is to be made. These means are provided in sufficient quantity to thoroughly cleanse and/or sterilize the area of skin of immediate concern. Typically, the kit will contain at least two, preferably at least three sterile swabs containing a cleansing or sterilization agent, such as betadine.

The sterile drape is of standard construction and is designed to adequately cover the joint of interest. Drapes useful in the practice of the protocol of this invention include those manufactured by Becton Dickinson & Co. The drape contains a hole to provide the attending physician with access to the knee and through which the needles may apply anesthesia and/or penetrate the knee joint to deliver anesthesia and to perform the lavage. While optional, use of a drape as part of the protocol is a preferred practice.

The first needle and syringe of the kit are for anesthetizing the skin and tissue over the joint. The needle and syringe are sized and equipped to perform this function, e.g., the syringe contains 5 cc of 1% xylocaine and the needle is 25 gauge by 1 ½ inches in length. Needles and syringes of other sizes can be used as desired as can other local anesthetics.

The second needle and syringe are sized and equipped to inject a second local anesthesia but in this case, the needle is also sized to perform the lavage. Typically, the needle is of 16 gauge by 1 ½ inches in length, and the syringe is of sufficient size to hold at least 50 cc of fluid. Like the first anesthesia, the second anesthesia can comprise any conventional local anesthesia (it can be the same as the first, or it can be different, e.g., a blend of 15cc of 1% xylocaine and 35cc of 0.25% bupivcaine).

The second needle and syringe are designed such that the syringe containing the second anesthesia can be replaced with a similar syringe containing the lavage fluid while the needle remains within the joint of the patient. Typically, the syringe containing the lavage fluid is of similar, if not identical, in design as the syringe containing the second anesthesia. The lavage fluid can vary to convenience, but typically it is a normal saline solution (e.g., 9 percent by weight of sodium chloride).

Preferably, each of the components of the kit described above are individually packaged in sealed, sterile containers and, optionally and preferably, all of the components as well as any optional components, are packaged in a sealed, sterile container such as a plastic tray with appropriate recesses for each component. Other appropriate sterile packaging includes bags or sacks, cartons and the like. Optional components include sterile gloves, hat and face mask for the attending physician, additional needles and syringes (filled with anesthesia or lavage fluid and/or empty) and protective bandaging to place over the puncture wound(s) created by the first and second needles.

The kit of this invention allows for the performance of a knee lavage in an out-patient setting, e.g., a clinic, physician's office, home or field environment, etc. Of course, regardless of the out-patient setting, the procedure is conducted within sterile confines and using sterile techniques.

The first step of the out-patient knee lavage protocol is the preparation of the knee. This is accomplished by applying the sterile betadine or similar cleansing agent containing swabs to the skin area through which the needles will enter the body. After the skin has been appropriately cleansed, the sterile drape is fitted over the knee such that the hole in the drape exposes the skin through which the needles will be inserted.

Using the first needle and syringe, local anesthesia is applied superficially to the joint using a suprapatellar lateral or other practitioner-desired approach using 5 cc of 1% xylocaine injected through a 25 gauge by 1 ½ inch needle to create a wheal. After allowing sufficient time (e.g., 30 seconds) for this first anesthesia to take affect, a second anesthesia is injected intra-articular through the wheal using the larger second needle (e.g., 16 gauge by 1 ½ inches). Typically, 30 cc of second anesthesia is injected from a pre-filled syringe consisting of 15 cc of 1% xylocaine combined with 35 cc of 0.25% bupivcaine. After sufficient time has passed to allow the knee joint to be fully anesthetized (e.g., about two minutes), the second syringe containing the second anesthesia is replaced with the third syringe containing the lavage fluid, e.g., 50 cc of normal saline combined with 500,000 units of polymyxin B antibiotic (to decrease the risk of infection). The second syringe is replaced with the third syringe while the second needle remains in the knee joint thus providing a closed system. The second needle is not removed from the knee joint until the lavage procedure is completed.

After the lavage fluid has been injected into the knee joint, it is slowly aspirated back into the syringe. In those situations in which the knee joint contains excessive fluid in the first instance, i.e., prior to the injection of any fluid from the kit, the excess fluid can be removed into the empty or partially empty second syringe from which the second local anesthesia was injected into the knee joint. Alternatively, if an empty syringe is provided with the kit, it can be used to capture the excess fluid. Once the lavage is completed, the second needle is removed from the knee joint, and the puncture wound at the wheal site is appropriately treated.

In one particular embodiment of this invention, the lavage protocol is used in combination with the conventional protocols for sodium hyaluronate or hylan G-F-20. In this embodiment, the knee joint is first subjected to a lavage which is followed one week later by the regime for the sodium hyaluronate or hylan G-F-20 (one injection per week over a three-five week period). This combined protocol has demonstrated improved results of viscosupplementation over the sodium hyaluronate or hylan G-F-20 protocol alone.

The kit and protocol of this invention allows physicians to perform therapeutic knee lavage in an out-patient setting. The protocol greatly reduces the cost associated with performing the lavage within a hospital setting, and it provides demonstrated relief to osteoarthritic joints. The protocol is fast, effective and sterile, and the kit is compact and simple.

Although the various embodiments of the invention have been described in considerable detail through the preceding specific embodiments, this detail is for the purpose of illustration. Many variations and modifications can be made by one skilled in the art without departing from the spirit and scope of the invention as it is described in the appended claims.

What is claimed is:

1. An out-patient, closed-needle joint lavage procedure comprising the steps of:

A. Preparing the joint by cleansing at least a portion of the skin covering the joint;

B. Covering the prepared joint with a sterile drape, the drape having an opening that is positioned over at least a portion of the cleansed skin;

C. Applying a first anesthesia superficially to the joint to create a wheal;

D. Injecting through the wheal a second anesthesia into the joint; and

E. Performing a lavage on the joint.

2. The procedure of claim 1 in which the joint is a human knee joint.

3. An improved sodium hyaluronate or hylan GF-20 protocol in which the improvement comprises performing the closed-needle lavage of claim 1 about one week prior to commencing either the sodium hyaluronate or hylan GF-20 protocol.

4. An out-patient, closed-needle joint lavage procedure comprising the steps of:

A. Preparing the joint by cleansing at least a portion of the skin covering the joint;

B. Covering the prepared joint with a sterile drape, the drape having an opening that is positioned over at least a portion of the cleansed skin;

C. Applying with a first needle a first anesthesia superficially to the joint to create a wheal;

D. Injecting through the wheal a second anesthesia with a second needle into the joint; and E. Performing a lavage on the joint using the second needle, wherein the second needle has not been removed from the joint.

5. The procedure of claim 4 in which the joint is a human knee joint.

6. An improved sodium hyaluronate or hylan GF-20 protocol in which the improvement comprises performing the closed-needle lavage of claim 11 about one week prior to commencing either the sodium hyaluronate or hylan GF-20 protocol.

* * * * *